United States Patent [19]
Ridgeway

[11] Patent Number: 5,967,975
[45] Date of Patent: Oct. 19, 1999

[54] HOME HEALTH PARAMETER MONITORING SYSTEM

[76] Inventor: Donald G. Ridgeway, 1852 Blacks Rd. SW., Hebron, Ohio 43025

[21] Appl. No.: 08/969,585

[22] Filed: Nov. 13, 1997

[51] Int. Cl.$^6$ ....................................................... A61N 5/00
[52] U.S. Cl. ............................................................. 600/300
[58] Field of Search ................................... 600/300, 301;
128/903, 904, 920, 921, 922, 923, 924;
340/870.09, 870.01, 870.16, 568, 309.25;
264/479.01, 569; 221/9, 15

[56] References Cited

U.S. PATENT DOCUMENTS

| | | | |
|---|---|---|---|
| 4,933,873 | 6/1990 | Kaufam et al. | 600/300 |
| 5,339,821 | 8/1994 | Fujimoto | 128/904 X |
| 5,576,952 | 11/1996 | Stutman et al. | 600/300 |
| 5,785,650 | 7/1998 | Akasaka et al. | 600/300 |

*Primary Examiner*—Samuel Gilbert

[57] ABSTRACT

A system for the automated remote monitoring of home health parameter measurement activities to assure outpatient subscriber compliance with prescribed measurement schedule regimen, and to alarm-monitor for off-normal measurements. Typical monitored health parameters include blood pressure, blood glucose level, clotting factor, and the like. The system comprises at least one subscriber remote station which interfaces with a communications link, and a central monitoring station also interfaced with the link and operative to receive and analyze messages transmitted by the remote station. The preferred remote station embodiment transmits measurement outcome messages to the central station each time an interconnected health parameter measurement device generates a signal indicating whether the current measurement is "normal" or "in-alarm", based on uniquely specified alarm criteria. Central station hardware/software verifies receipt of such signals within each of the subscriber's uniquely scheduled measurement time windows, and alerts alarm dispatchers to take pre-specified action if a scheduled measurement is forgotten. Dispatchers are also alerted if "in-alarm" measurements occur. Alternative remote station embodiments accept monitoring device signals corresponding to health parameter measured values. One alternative embodiment performs alarm monitoring in the remote station, another performs alarm monitoring at the central station. All embodiments provide subscribers with help-buttons to initiate transmission of alarm messages to the central station in event of emergency. Since the central station is alerted if any scheduled measurement is missed, no immobilizing emergency can go undetected longer than the maximum time between consecutively scheduled measurements.

12 Claims, 5 Drawing Sheets

HOME HEALTH PARAMETER MONITORING SYSTEM

BACKGROUND—CROSS-REFERENCES TO RELATED APPLICATIONS

This invention utilizes a time window compliance monitoring methodology similar to the methodology disclosed in my "SELF-MEDICATION MONITORING SYSTEM" Application Ser. No. 08/507,546, filed Jul. 26, 1995, U.S. Pat. No. 5,710,551.

BACKGROUND—FIELD OF INVENTION

This invention relates generally to the monitoring and supervision of outpatient compliance with prescribed regimen, and more specifically to the automated remote monitoring and supervision of outpatient in-home health parameter monitoring activities.

BACKGROUND—FIELD OF INVENTION

In the not-too-distant-past, physicians commonly monitored patient well-being via health parameter measurements made during regularly scheduled office visits. During recent years, however, steadily increasing healthcare costs and outpatient populations have created a need to maximize time intervals between office visits. As a result, a number of vital health monitoring functions once directly performed by nurses and physicians have largely become patient self-care responsibilities. Large numbers of physicians now regularly prescribe home-monitoring of such health parameters as blood pressure, heart rate, blood glucose level, and clotting factor.

In theory, prescription of home-monitoring of health parameters puts health maintenance responsibility squarely where it belongs, and should reliably provide physicians with greatly expanded feedback visibility and enhanced "tuning" ability to continuously maintain optimum treatment efficacy. In practice, however, patient compliance with prescribed self-measurement regimen can't be expected to be any better than compliance with prescribed drug regimen. Although self-medication compliance is also clearly in patients' best interests, the National Pharmaceutical Council estimates that noncompliance with prescription drug regimen causes a whopping 30% to 50% failure rate in achieving desired clinical results[1] concurrently adding roughly $100 billion to America's managed care costs[2].

REFERENCES CITED IN THE PRECEDING PARAGRAPHS

1. Cardinale V. "Noncompliance, A Major Hurdle In Integrated Health Systems". *Drug Topics*. May 22, 1995, v139 n10 p35(2)
2. Mandelker J. "Monitoring Drug Compliance Can Reduce Total Medical Plan Costs". *Business & Health*. May 1993, v11 n6 p26(7).

Noncompliance with prescribed home-monitoring regimen is also a massively expensive problem. But although it happens a lot, it's also been very hard to detect. For example, assume that a physician prescribes self-monitoring of blood pressure for a hypertensive patient, to be performed daily between the hours of 6 am and 9 am, with results to be recorded in a written log. During the next office visit, the patient presents a written record of daily blood pressure measurements made since the last visit, all falling within a "normal" range. But how can the physician be sure they're really valid? In reality, some of the measurements may have been forgotten during morning hours, and made in the afternoon or evening when blood pressure is classically lower. And who's to know if some, most, or even all measurement entries may be 100% fictional . . . there's really been no way for the attending physician to be sure.

In other scenario's, a physician may ask a patient to perform home-measurement of a health parameter whenever the patient senses a need, or based on other criteria, and to maintain a written log of such measurement activities. The physician may gain greatly enhanced diagnostic insight and ability to "tune and optimize" treatment regimen if the patient is fully compliant But quality of treatment can be no better than quality of feedback data. Were all of the measurements actually made, or were some logged entries fictional? If real, were measurements really made at logged times? Were actual measurement values consistently recorded, or were problem-level entries modified to fall within a normal range?

Patient penalties for self-measurement noncompliance can be both costly and devastating, and the pressing need to monitor such compliance has been well recognized. Some of the leading monitoring device manufacturers have begun adding an automatic measurement history logging feature, which internally stores records of the last "n" health parameter measurements. Measurement records can later be reviewed on demand, usually by inputting the stored data to a personal computer via a serial or parallel interface port.

In a best-case scenario, such history data reviews merely provide attending physicians with quantitative chronologies showing how good (or bad) home-measurement compliance was over a given timeframe. But it's history data, and it's probable that data reviews performed posthumously may sometimes reveal a series of unheeded alarm-level health parameter measurements, culminating in death of the patient. Such tragedies could generally be averted if automated alarm monitoring promptly alerts physicians whenever "in-alarm" health parameter measurements occur.

To date, however, automated monitoring solutions have been both costly and complex. For example, a "Home Medical System" concept disclosed by Fujimoto in U.S. Pat. No. 5,339,821 utilizes a sophisticated interactive in-home terminal for transmitting measurements of such parameters as blood pressure, heart rate, body temperature, and EKG readings to a remote host computer. The system further enables an automated preprogrammed interactive diagnosis dialog between patient and host computer. A similarly costly/complicated system implementation has been introduced by HealthTech Services Corporation of Northbrook, Ill. It's HANC robotic terminal utilizes voice synthesis and sophisticated artificial intelligence to step home patients through preprogrammed self-care sequences, enforce self-medication and home-monitoring compliance, and there can even be two-way audio/visual communication between patient and medical staff at a central healthcare facility.

Many patients regard such monitoring system complexities as intimidating, particularly elderly patients. That's a major drawback, in that patient intimidation can seriously limit system effectiveness. It's well recognized that any monitoring system's success is highly dependent on patient acceptance and cooperation. And while such monitoring systems may be affordable in a few special cases, they're prohibitively expensive for monitoring compliance for the vast majority of ambulatory outpatients who regularly self-measure health parameters via prescribed monitoring devices obtained from pharmacies. To assure compliance for the ambulatory masses, all that's really needed is inexpensive automated telehealth methods to verify that home-measurement activities are performed at prescribed time intervals, with real time alarm-monitoring of measurement values, and with automatically logged measurement results protected from patient manipulation.

Paradoxically, telemedicine developers have to date leaned toward more costly/cumbersome data overkill. There's been a common tendency to bombard physicians with streams of measurement data, including large percentages of data representative of "normal" conditions. But in many cases, exception reporting can minimize both data transfer requirements and physician data review time. In reality, physicians seldom have much need to review health parameter measurement values fluctuating within a "normal" range of variation. For most outpatients, it's sufficient to provide no more than an automated method for assuring that home-measurement activities are being performed at prescribed time intervals, with limit-checking to assure prompt physician notification if parameter measurements go "in-alarm", and with automatic logging of all measurement outcomes. Such a methodology can be implemented via inexpensive hardware and software that's widely used in fire and burglar alarm systems.

In fire and burglar alarm systems, alarm sensors at monitored sites typically produce contact closure signals, which cause an on-site digital communicator to responsively transmit digitally encoded alarm messages to a central monitoring station, usually by means of the interconnected telephone network. Central stations have extensive alarm monitoring capabilities, including means to monitor the opening and closing of businesses within specified time windows. Such open/close monitoring capabilities are usually readily adaptable to assuring that health parameter home-measurement is continually performed within time windows of width and spacing optimized to best suit unique patient needs. And virtually all health parameter measurement device categories either have or can be provided with limit-checking capabilities, such that simple "normal" vs. "in-alarm" electrical signals can serve as monitoring system inputs which can be processed via standard central station alarm/status point processing techniques.

Central stations also commonly maintain computer databases which can contain comprehensive information on each monitored subscriber, including phone numbers for responders, police, fire department, ambulance service, and the like. Most databases can also routinely include medically-related information paramedics might need if summoned to respond to a medical emergency.

All telecommunications hardware/software system building blocks needed for cost-effective automated monitoring of outpatient compliance with in-home health parameter measurement regimen thus exist in pre-proven form. This application discloses a monitoring system methodology, and presents an easily constructed system implementation comprised of readily available hardware/software building blocks.

The preferred design embodiment described herein incorporates well known security system apparatus into the design of a "subscriber remote station" which accepts "normal" and "in-alarm" electrical signal inputs from health parameter measurement devices, and responsively transmits corresponding messages to a typical security system central station, programmed to alarm monitor for "in-alarm" measurements, and to assure that all in-home health parameter monitoring activities are performed within prescribed time windows. The central station's computer also automatically creates and stores a data record for each health parameter measurement. Printouts of such data records can provide physicians with an accurate chronology of in-home health parameter measurement activities, with no possibility of patient manipulation of stored data.

A number of security system manufacturers offer digital communicators suitable for incorporation into an effective system design. As a bonus feature, such digital communicators can also monitor input signals from simple pushbutton switches, often referred to as "help-buttons". There's also normally an ability to extend "help-button" protection to include portable miniature wireless RF transmitters, commonly worn as a neck pendant, belt-mounted, or worn on a wristband. And contact closure signals from a range of in-home healthcare equipment types can be connected to spare input points for very economical auxiliary alarm monitoring.

Accordingly, the system design embodiments described herein can easily be optionally provided with both built-in and portable help-button capabilities commonly found in emergency response systems. With or without such capabilities, however, this new methodology adds an important new dimension to emergency response protection. Outpatient well-being can often be inferred as a by-product of indication that "normal" in-home health parameter measurements are being made per prescribed schedule. Central station alarm dispatchers will promptly initiate follow-up procedures any time a health parameter measurement is either "in-alarm" or isn't received by the central station when due.

The longest time any kind of in-home emergency might go undetected is therefore the maximum time between consecutively scheduled health parameter measurements. Availability of this new technology will therefore both maximize home-monitoring compliance, and provide welcome peace of mind for large numbers of outpatients living alone in fear of lying helpless for days as an undetected immobilizing mishap turns into a tragedy.

OBJECTS AND ADVANTAGES

Accordingly, several objects and advantages of the present invention are:

(a) to provide a reliable apparatus and method for the automated remote monitoring and supervision of outpatient subscriber compliance with prescribed health parameter home measurement regimen;

(b) to provide subscribers with optional latitude to perform health parameter measurement activities within time windows of specifiable width, or to pace measurement activities based on other criteria;

(c) to provide prompt detection of forgotten health parameter measurements, so that timely follow-up can restore subscriber compliance with minimal deviation from prescribed schedules;

(d) to provide alarm monitoring for health parameter measured values which are "in-alarm", based on uniquely specified "normal" health parameter measurement ranges;

(e) to automatically log all subscriber home health parameter measurement activities, and maintain stored measurement data protected from subscriber modification;

(f) to provide a simple system design with a low overall cost, in order to make the apparatus and monitoring affordable for a maximum number of subscribers; and (g) to provide a design which is easy to use, non-intimidating, and non-demeaning, particularly for elderly subscribers.

Other objects and advantages are:

(h) to automatically verify subscriber well-being as a byproduct of the monitoring of subscriber home health parameter measurement activities;

(i) to provide subscribers with effective help-button means to alert the central monitoring station if help is needed in event of an emergency of any kind; and () to automatically provide frequent verification of proper system operation as a by-product of the monitoring of subscriber home health parameter measurement activities These and other objects and advantages of the present invention will become apparent from a consideration of the ensuing description and drawings.

DRAWING FIGURES

This invention will be more fully understood by reference to the accompanying drawings, in which.

REFERENCE NUMBERS USED IN DRAWINGS

| 1 | enclosure box | 11 | one-line modular plug |
|---|---|---|---|
| 2 | digital communicator | 12 | Y-connector splitter |
| 3 | AC adapter | 13 | feed-through grommets |
| 4 | signal input jack panel | 14 | help-button RF transmitter, optional |
| 5 | 1-channel RF reciever, optional | 15 | built-in help-button switch |
| 6 | switch mounting panel | 16 | power-on LED indicator |
| 7 | on/off switch | 17 | cover plate |
| 8 | terminal strip | 18 | keyboard |
| 9 | DC power cord. | 19 | LCD display |
| 10 | communications cord | 20 | portable programming terminal |

DESCRIPTION—FIGURES 1 TO 3

In accordance with the present invention, a home health parameter monitoring system is disclosed. The system is primarily intended for use by outpatients, as subscribers to a monitoring service, and home health parameters are typically self-measured. The words "subscriber" and "outpatient", as well as the terms "self-measurement" and "home-measurement", are therefore used interchangeably throughout the wording of this patent application.

Figure 1:
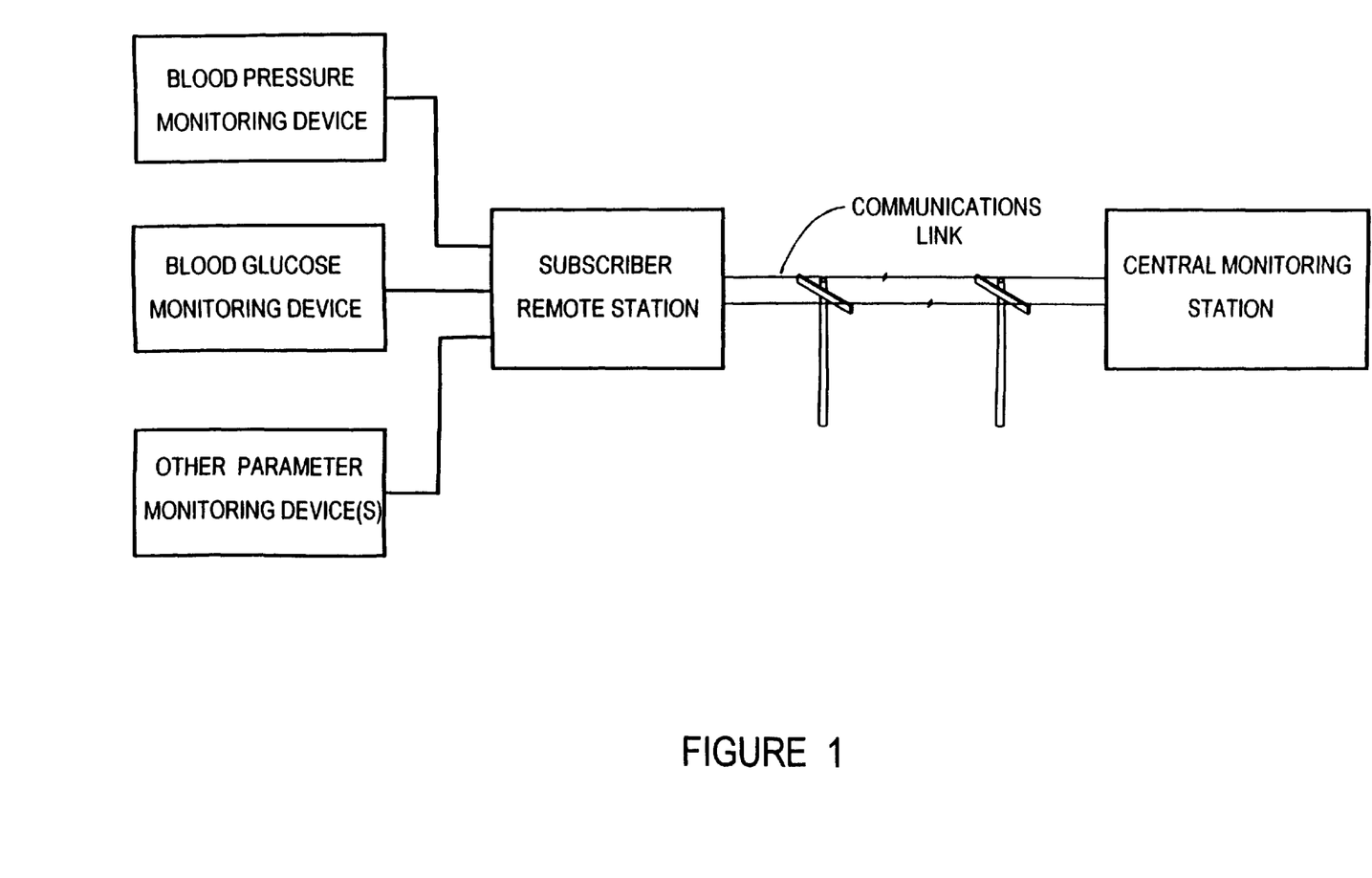
FIG. 1 is a functional block diagram showing a communications link interface between a typical subscriber remote station and a central monitoring station.

A functional overview of the system is presented in FIG. 1, which shows a subscriber remote station interconnected to a central monitoring station via a communications link. Subscriber remote stations are typically located in homes of outpatients whose physicians have prescribed periodic in-home monitoring of one or more health parameters. The central station is typical of central stations widely used in the Security Industry to monitor fire and burglary alarm systems in homes and businesses.

The communications link is normally the interconnected telephone network, but may also comprise a satellite communications link, a cable television communications link, a radio frequency communications link, a directly wired communications link, or any other suitable media for transmission of messages from a subscriber's home to the central station.

FIG. 1 also illustrates that subscriber remote station embodiments described herein can concurrently interface with a number of health parameter monitoring devices. In other embodiments, one or more health parameter monitoring devices and remote station functions could be combined in an integrated package. Health parameters which are now commonly self-monitored at home include blood pressure, heart rate, blood glucose level, and clotting factor. It's likely that additional health parameters may become commonly self-monitored at home, as lengthening patient lifespans and economic necessity continue to force physicians to prescribe increasing self-care responsibility.

Irrespective of health parameter, interfacing monitoring devices are assumed to have simple built-in limit-checking capabilities. For example, assume that a physician designates that systolic blood pressure should not exceed 160 mm Hg for a given patient. Procedures similar to those used to set digital alarm clocks would be used to set an upper alarm limit in the monitoring device. Systolic blood pressure measurements of 160 mm Hg or more would then cause the monitoring device to generate an "in-alarm" signal output, while measurements of less than 160 mm Hg would cause generation of a "normal" signal output. Simple dry contact "normal" and "in-alarm" signal outputs are easily accommodated by the preferred subscriber remote station embodiment.

Health parameter measurement values are commonly limit-checked in hospital intensive care wards, such that audible and visual alarm annunciation is triggered at a centrally located nurse station whenever a monitored health parameter measurement is "in-alarm". Low-cost prescription monitoring devices designed for home use, however, typically do not yet have similar limit-checking capabilities. It's because there's been no real need to date. But prescription monitoring device manufacturers which include Behringer-Mannheim, Lifescan, and Omron have expressed willingness to consider modifying their designs to incorporate limit-checking capabilities and dry-contact signal outputs, in anticipation of massive sizes of markets which could be made available by the present invention.

Figure 2:
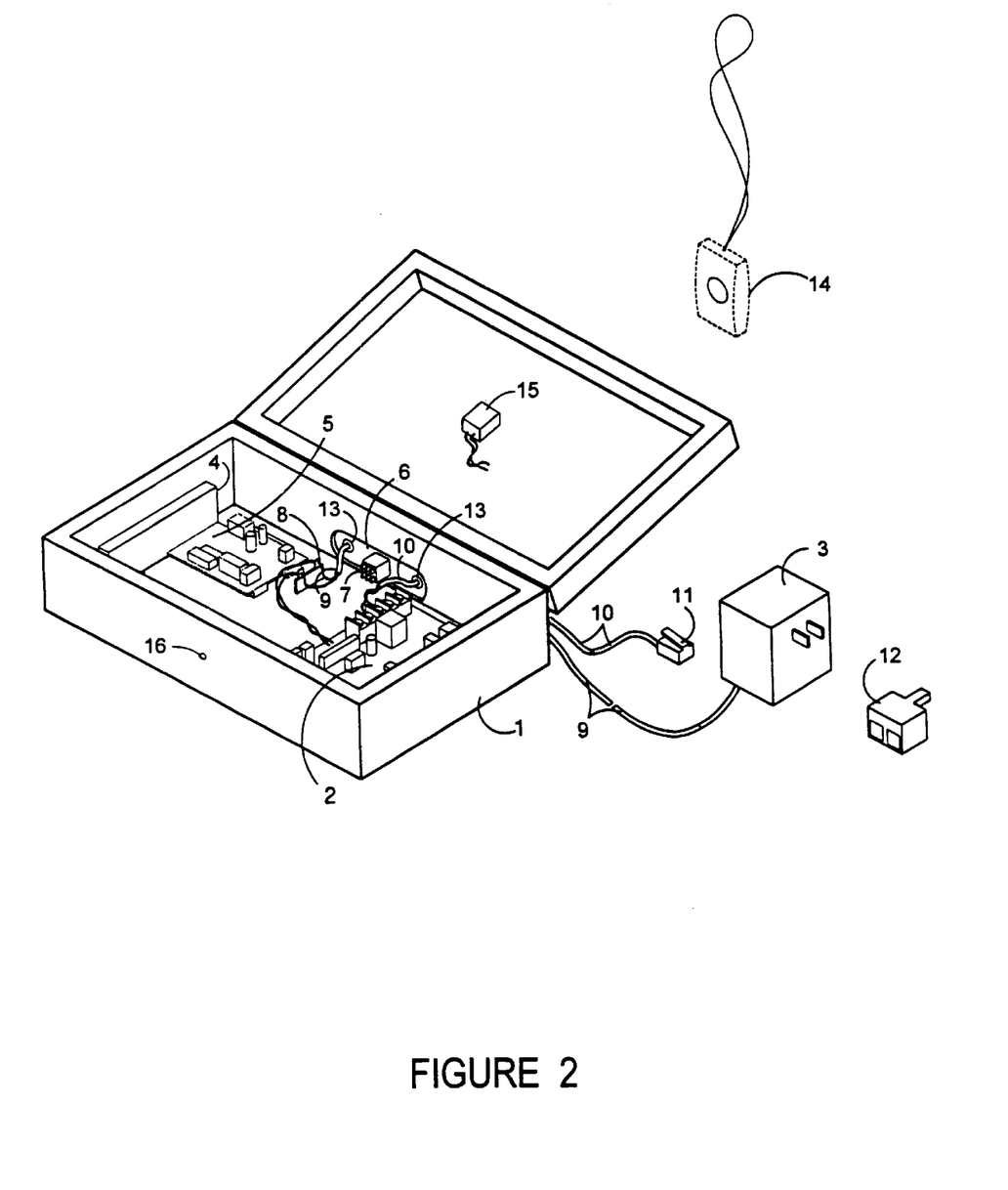
FIG. 2 is an isometric view of an easily constructed preferred embodiment of a subscriber remote station.

FIG. 2 illustrates the preferred subscriber remote station design embodiment, comprised of readily obtainable components. A simple enclosure box 1, equipped with either a hinged or removable top, must be large enough to accommodate a digital communicator 2, a signal input jack panel 4, and an optional 1-channel RF receiver 5. The proposed construction for box 1 is attractively finished wood or plastic, which will allow radio signals from an optional help-button RF transmitter 14 to pass through and be received by optional receiver 5.

Digital communicators are available as standalone products from a number of security system manufacturers, including Scantronic, C & K Systems, Linear Corporation, and Visonic Ltd. In security systems, digital communicators typically accept voltage signals generated by alarm sensor contact closures, and responsively transmit encoded alarm messages to central monitoring stations, usually via the interconnected telephone network. Encoded messages identify both monitored site location and the point number(s) assigned to the sensor(s) that signaled the alarm condition (s). Capacities of 4, 8, or 16 input points are typical for small digital communicators best suited for this application.

An AC adaptor 3 plugs into a standard wall outlet, and converts AC line voltage to a suitable DC voltage, typically 12 VDC in security system applications. A DC power cord 9 passes through a feed-through grommet 13 and terminates on+and–lugs on a terminal strip 8 for convenience in distributing DC power within box 1. A two-conductor communications cord 10 passes through a feed-through grommet 13 and terminates on "tip" and "ring" terminals on digital communicator 2. The other end of communications cord 10 is terminated in a standard 1-line modular plug 11. Connection to telephone wiring in a subscriber's home is made by inserting modular plug 11 into a standard phone jack. A standard Y-connector splitter 12 can be used to allow a 1-line house phone and modular plug 11 to share the same phone jack.

A patient can summon help in event of an emergency by means of either a built-in help-button switch 15 or optional help-button RF transmitter 14. Switch 15 is a SPST momentary push-button switch, which responsively applies a voltage to one of digital communicator 2's input points when pressed. Optional RF receiver 5 is a small 1-channel unit, equipped with an output relay which responsively applies a voltage signal to one of digital communicator 2's input points upon receipt of a radio signal from optional transmitter 14. Both receiver 5 and transmitter 14 can be obtained from suppliers such as Visonic Ltd.

A switch mounting panel 6 made of thin plastic or phenolic sheet stock is recess-mounted in a cutout in the back of box 1 to minimize protrusion of an on/off switch 7's toggle lever, thereby minimizing chances of accidental "bumping" on or off. Switch 7 is a low-profile DPST toggle switch which enables or disables DC power for signal input loops. A power-on LED indicator 16, recess-mounted in the front of box 1, glows to indicate that switch 7 is "on" and DC power is being supplied to signal input loops. All installed help-button capabilities are always operational, irrespective of position of switch 7.

Contact closure signal inputs from health parameter monitoring devices interface with the subscriber remote station via multi-pin connectors which plug into side-mounted signal input jack panel 4. Input jack panel functionality can be optionally expanded to include a capability to accept contact closure signals from other types of health care equipment. Input jacks are wired into digital communicator 2's input channel terminals. EN3™ mini-connectors by Switchcraft, often used in medical applications, are a good choice here.

During development of this invention, a prototype subscriber remote station was built, with component locations essentially as shown in FIG. 2. Digital communicator 2 and 1-channel RF receiver 5 were secured to the bottom of box 1 by adhesive backed hook & loop fastener strips. Enclosure box 1 was an attractive ornamental wood design, selected for in-home placement on shelf-, counter-, or table-top, with external dimensions of approximately 7"×3"×13". Digital communicator 2's "trip/return" output terminal was wired to one of its input points, such that a "ready" message is automatically transmitted to the central station when AC adapter 3 is plugged in and on/off switch 7 is turned "on".

The optional in-home-measurement schedule compliance verification function could be incorporated in a subscriber remote station design, but all embodiments described herein verify schedule compliance at the central station. Although compliance verification programs are not difficult to develop, standard central station computer techniques widely used to monitor the opening and closing of businesses are usually easily adapted to implement the present invention's measurement time window monitoring methodology, wherein in-home health parameter measurement activities are scheduled for performance within periodic time windows which can be uniquely defined for each subscriber.

In security system applications, many business owners and managers want to be sure that their establishments are opened for business within a prescribed time window on the morning of every business day. They similarly want to be sure that closing occurs within a prescribed evening time window. Central station alarm dispatchers are automatically alerted if an opening signal isn't received within the morning opening time window, if a closing signal isn't received within the evening closing window, and if opening or closing signals are received at improper times. The ability to monitor multiple open/close time windows of varying timing and width is usually provided.

Figure 3:
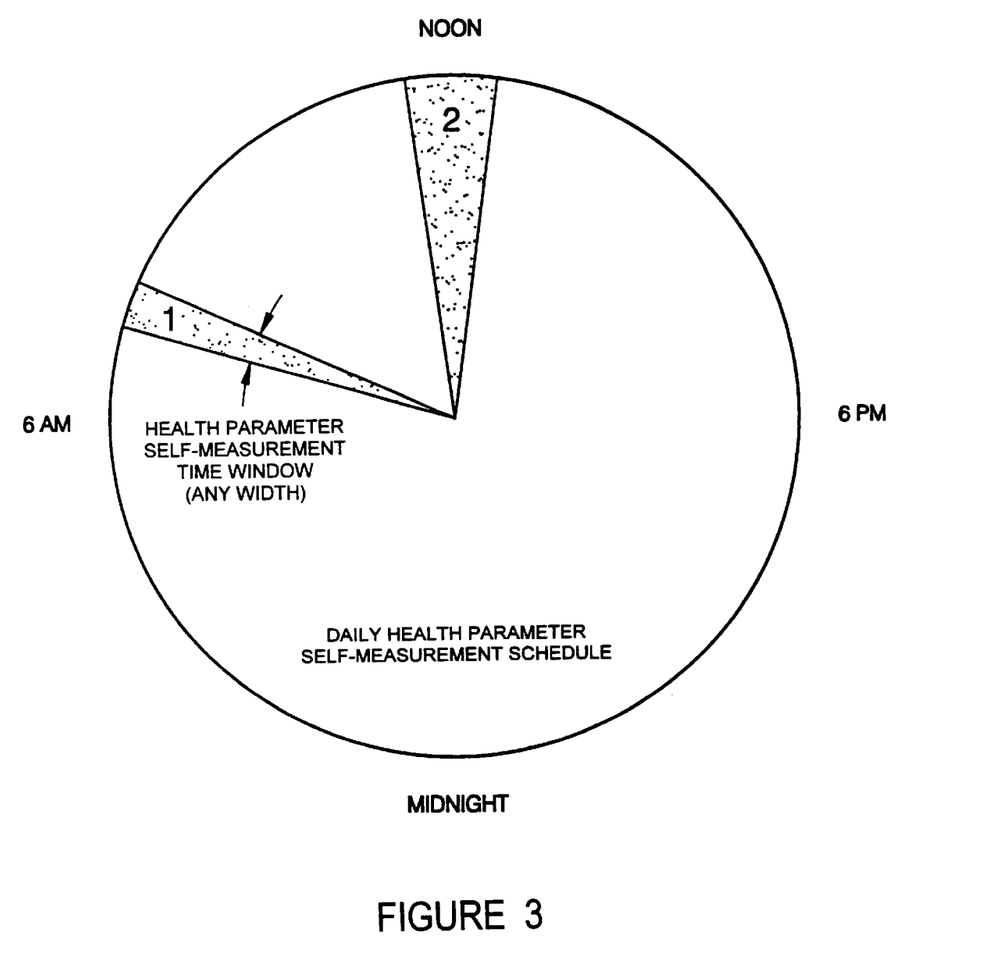
FIG. 3 illustrates the concept of self-measurement time windows utilized in the disclosed automated monitoring methodology.

As commonly done for business openings and closings, optional definition of subscriber-unique self-measurement time windows is hence part of the subscriber database record creation process at the central station. FIG. 3 illustrates a typical daily schedule consisting of two self-measurement time windows, which can be of the same or varying width. Self-measurement timing and width (time tolerance) for time windows is uniquely established by each subscriber's attending physician. The central station computer monitors each time window to assure receipt of either a "normal" signal or an "in-alarm" signal within each scheduled time window. Dispatchers will promptly initiate follow-up sequences if a time window closes without receipt of either kind of signal, or if an "in-alarm" signal is received at any time.

In some cases, physicians may not want selected patients to always (or ever) perform self-measurement activities within prescheduled time windows. In such cases, they may instead prescribe self-measurement of health parameters whenever the patient senses a need to do so, or based on other criteria. In any case, all self-measurement activities are automatically logged in central station bulk memory, with each measurement record minimally including date, time, and "normal" vs. "in-alarm" measurement outcome. Printed chronologies of self-measurement activities during specified timespans can be provided by most central stations at token cost.

Normal system operation implicitly provides frequent verification of the monitoring system's operational status. Central station dispatchers promptly initiate follow-up sequences whenever a self-measurement signal is not received within a scheduled time window, irrespective of reason why.

System equipment failures, as well as power and communications link outages, are hence detected the first time a scheduled measurement time window closes without receipt of a valid measurement signal.

The design embodiments described herein provide early detection of most hardware/software malfunctions which would block proper monitoring system operation. Most such malfunctions would not be as reliably detected by alternative design embodiments which incorporate both limit-checking and time window monitoring functions in the design of a subscriber remote station, reporting to a central station only in event of alarm detection. At the central station, absence of communication messages from such embodiments could mean full compliance and 100% "normal" health parameter measurements . . . or, could be due to some form of system failure.

It'd be impossible to tell the difference at the central station, unless the remote station was designed to periodically transmit "ready" signals to confirm operational status. But if sent at meaningful frequency, "ready" signals would generate about the same level of communications traffic as the three embodiments presented herein. Also, such an embodiment would complicate field installation activities, and transference of vital system intelligence functions from a computer room environment to thousands of homes would diminish overall system reliability. The added cost of "smarter" remote station embodiments would therefore be an imprudent investment.

DESCRIPTION OF ALTERNATIVE EMBODIMENTS—FIGS. 2, 4, AND 5

Figure 4:
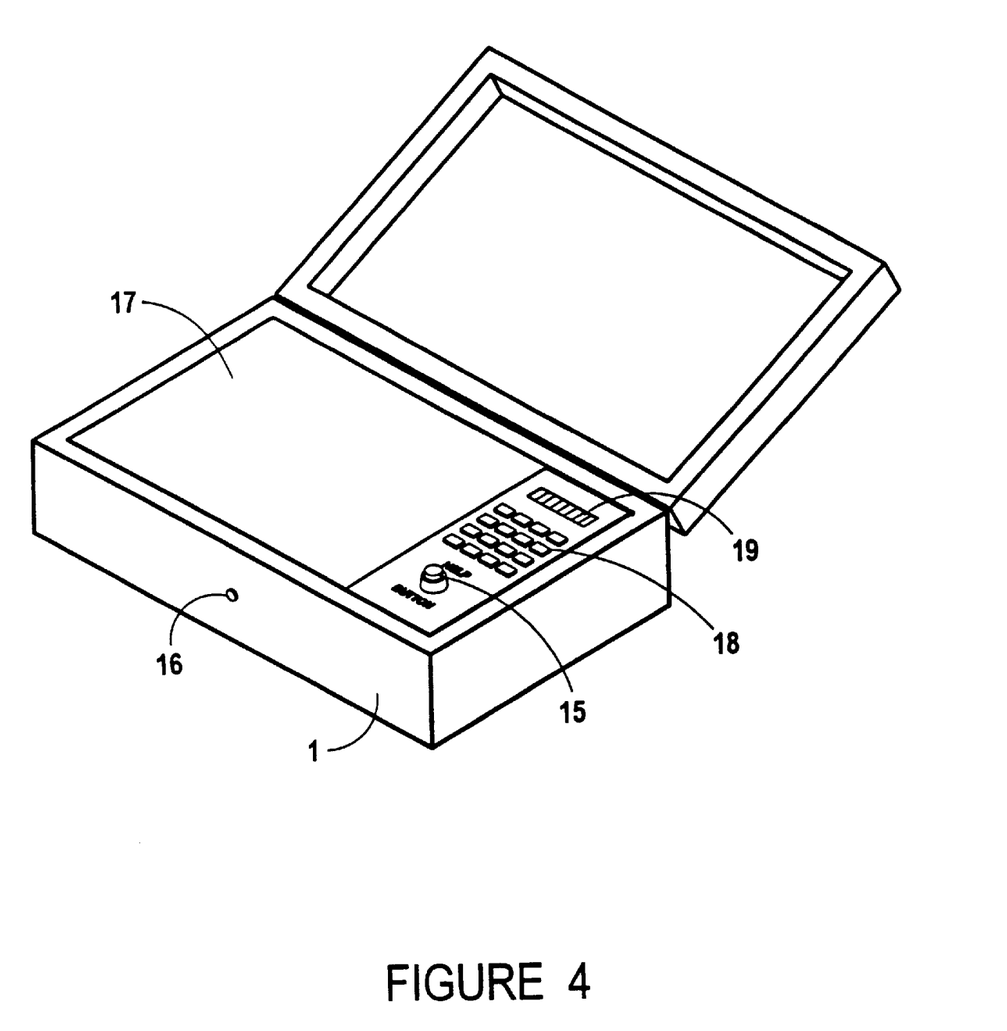
FIG. 4 is an isometric view of alternative subscriber remote station embodiment "A", which incorporates a built-in LCD display and keyboard in addition to the ability to limit-check health parameter measurement signals.

A subscriber remote station design implementation for an alternative embodiment "A" is illustrated in FIG. 4. In this embodiment, health parameter monitoring devices provide the remote station with electrical signals corresponding to health parameter measured values. A keyboard 18 and a LCD display 19 are used to accept limit-check entries for each monitored health parameter. A cover plate 17 protects components mounted inside enclosure box 1.

When a measurement signal is inputted to the remote station by a health parameter monitoring device, a signal multiplexer passes a digital representation of the health parameter's measured value to a signal processing module, which performs limit-checking, and provides a communicator module with an outcome signal corresponding to either a "normal" or "off-normal" measured value. The communicator module converts the outcome signal to a digital outcome message, and transmits it to the central station via the communications link.

The health parameter's measured value may also be transmitted to the central station. Central station message processing is the same as in the preferred embodiment, with exception to the fact that stored measurement data records may also include health parameter measured values.

Figure 5:
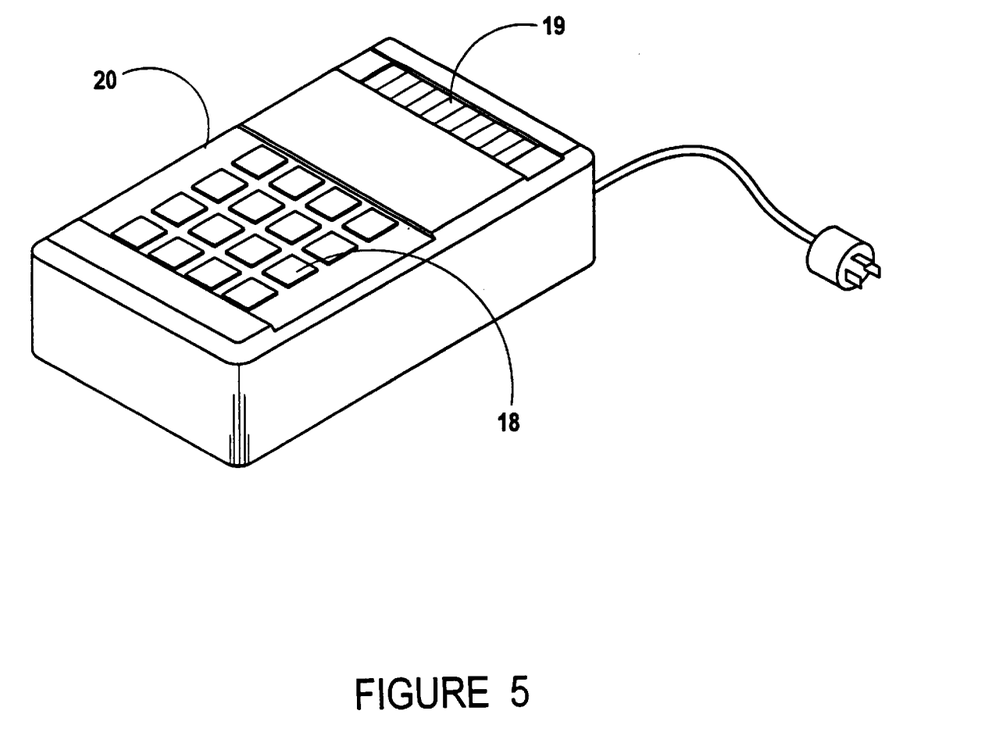
FIG. 5 presents the general appearance of a portable programming terminal which can be plug-connected to an economized version of subscriber remote station embodiment "A".

Embodiment A's remote station design can be economized by relocation of keyboard 18 and LCD display 19 to a portable programming terminal 20, which can be shared by many remote stations. Portable programming terminal 20 is plug-connected to remote stations only during entry of limit-check settings. A jack to accommodate plug connection could be mounted in switch mounting panel 6. In addition to reducing remote station cost and complexity, removal of built-in keyboard and display capabilities provides a more secure, "patient-proof" design, in that only health care professionals have the ability to make or modify limit-check settings.

A subscriber remote station for an alternative embodiment "B" also accepts input signals corresponding to health parameter measured values, but does not perform limit-checking. Embodiment B's remote station is similar to the preferred embodiment in appearance. When a measurement signal is inputted to the remote station by a health parameter monitoring device, a signal multiplexer passes a digital representation of the health parameter's measured value to a signal processing module, which provides a communicator module with a signal corresponding to the health parameter's measured value. The communicator module then transmits a digital measured value message to the central station via the communications link. Central station message processing functions are the same as for the preferred embodiment and alternative embodiment "A", except that the central station additionally performs limit setting entry and limit-checking functions. Stored measurement data records include health parameter measured values.

OPERATION—FIGS. 2, 3, 4 AND 5

A discussion of operation of this invention properly begins with programming which precedes installation of a subscriber remote station at an outpatient subscriber's home. Referring to FIG. 2, in all embodiments a digital communicator 2 must be programmed to properly communicate with the central station. The programming process basically loads a few customizing parameter entries into non-volatile memory.

Customizing parameters are typically entered into digital communicator 2 by programming a EEPROM chip or by plugging modular plug 11 into either a special programming terminal or a modem port in a PC loaded with special programming software. Digital communicator manufacturers provide such EEPROM programmers, programming terminals, and special PC software, along with simple "cookbook" procedures which facilitate entry of customizing parameters, such as primary and backup central station phone numbers, phone number at the subscriber's home, account number assigned to the subscriber, message format selection, and a range of parameters which customize processing for each input point.

In the preferred embodiment, health parameter monitoring devices provide the subscriber remote station with measurement outcome signals, indicating that health parameter measurements are either "normal" or "in-alarm". In alternative embodiment "A", monitoring devices provide the subscriber remote terminal with signals corresponding to health parameter measured values, and limit-checking is performed within the remote station. Referring to FIG. 4, keyboard 18 and LCD display 19 are used to enter limit-check settings for each measured health parameter prior to commencement of monitoring. Alternatively, a portable programming terminal as illustrated in FIG. 5 is plugged into an economized version of the embodiment "A" remote station to allow entry of limit-check settings. In all embodiments, an account database record must also be created at the central station prior to commencement of monitoring. Central stations which monitor security systems have database structures readily adaptable to the monitoring of health parameter home measurement activities. Standard database fields include subscriber name, address, and phone number, names and phone numbers of designated responders, and phone numbers for cognizant police, fire department, ambulance service, family physician, and hospital of choice. Provisions are also typically made to allow entry of medical history which paramedics might find invaluable, if called to respond to a medical emergency.

In all design embodiments, health parameter measurement time windows may also be predefined at the central station as part of the database record creation process. Alternatively, an attending physician may wish to pace subscriber home health parameter measurement activities based on other considerations. FIG. 3 illustrates a typical daily health parameter measurement schedule consisting of two measurement time windows. Each time window is uniquely defined by a start time and a stop time, and time window widths can either vary or be the same. Compliance with health parameter home measurement schedule regimen is monitored via automated verification that valid health parameter measurement signals are received within each scheduled measurement time window. In both the preferred embodiment and embodiment "A", the subscriber remote station provides the central station with limit-checked measurement results data, wherein health parameter measurements are either "normal" or "in-alarm". In embodiment "B", however, limit checking is performed at the central station. Limit settings must therefore be defined for each monitored health parameter as part of the central station database record creation process.

Once the preceding set-up procedures have been accomplished, installation at a subscriber's home can be made in a matter of minutes. Referring to FIG. 2, enclosure box 1 is first placed in a location of choice, typically on a table-top, counter-top, or shelf. Health parameter measurement devices to be monitored are next plug-connected via the remote station's signal input jack panel 4. Connection to in-home telephone wiring is then made by plugging modular plug 11 into a standard phone jack. If necessary, a Y-connector splitter 12 can be used to let modular plug 11 and a one-line house phone share the same phone jack.

Finally, AC adapter 3 is plugged into a wall outlet, and switch 7 is turned "on". As digital communicator 2 powers-up, it automatically transmits a "ready" signal to the central station via the communications link. A phone call is then made to the central station to verify that a "ready" signal has been received, and to notify dispatcher staff that the new installation is about to be tested.

Testing commences with pressing built-in help-button switch 15. If present, optional miniature RF wireless transmitter 14's help-button is also pressed. Next comes performance of any tests that may be uniquely specified for each interconnected health parameter monitoring device. A phone call is then made to the central station to verify proper receipt of all test signals.

Monitoring system operations are transparent to subscriber-users. Subscribers are simply responsible for performing prescribed health parameter measurements per prescribed schedule regimen. FIG. 3 illustrates a predefined health parameter measurement schedule consisting of two daily measurement time windows. Each subscriber can have uniquely scheduled measurement time windows, and time windows can be of the same or unique width. Dispatchers are promptly alerted to take appropriate action upon detection of any of the following occurrences:

a) A valid health parameter measurement signal is not received within a scheduled time window.

b) A health parameter "in-alarm" signal is received, at any time.

c) A help-button signal is received at any time, whether initiated by built-in help-button switch 15 or by optional help-button transmitter 14.

Occurrence "a" usually indicates that a scheduled health parameter measurement has been forgotten, the most common compliance error. A prompt central station dispatcher follow-up phone call can usually remind the subscriber to make the missed measurement before much time elapses. Alternatively, occurrence "a" could be an indication that the subscriber has been immobilized by an accident, stroke, heart attack, or other debilitating medical emergency. In such cases, failure to reach the subscriber via phone immediately prompts dispatcher initiation of uniquely predefined emergency response procedures.

Occurrence "b" means that a health parameter measurement is outside a "normal" range, as uniquely defined for the monitored outpatient, whereupon central station dispatchers promptly initiate uniquely predefined response procedures. Occurrence "c" always prompts dispatchers to immediately initiate uniquely predefined emergency response procedures.

In the more serious emergencies, however, subscribers are often incapable of pressing a help-button. Every year thousands of senior citizens lose their lives at home simply because nobody knows they need help . . . some lie helpless for days. As a valuable "side-benefit", all embodiments of this invention prevent occurrence of such scenarios. It is readily apparent that the longest time that any kind of subscriber emergency might go undetected is the maximum time between consecutively scheduled health parameter measurements. Central station alarm dispatchers will follow-up promptly the first time a scheduled measurement is missed, for whatever reason.

SUMMARY, RAMIFICATIONS, AND SCOPE

Accordingly, the reader will see that this invention provides a reliable apparatus and method for the automated remote monitoring and supervision of outpatient subscriber compliance with prescribed health parameter home measurement regimen. It assures that health parameter home measurements are performed per prescribed schedule, and also promptly alerts central station alarm dispatchers when health parameter measurements are "in-alarm", based on uniquely specified "normal" health parameter measurement range(s). It concurrently assures that any form of emergency which renders a subscriber helpless cannot go undetected longer than the maximum time between consecutively scheduled health parameter measurements. These combined capabilities offer a welcome extension of the duration of an independent lifestyle for a great many of the elderly and infirm. Furthermore, this invention offers additional advantages in that it provides subscribers with optional latitude to perform health parameter measurement activities within time windows of specifiable width, or to pace measurement activities based on other criteria;

it provides prompt detection of forgotten health parameter home measurement activities, so that timely alarm dispatcher follow-up can restore compliance with minimal deviation from prescribed schedules;

it automatically logs all subscriber home health parameter measurement activities, and maintains stored measurement data protected from subscriber modification;

it provides a simple system design with a low overall cost, in order to make the apparatus and monitoring affordable for a maximum number of subscribers;

it provides a design which is easy to use, non-intimidating, and non-demeaning, particularly for elderly subscribers;

it provides subscribers with effective help-button means to alert the central monitoring station if help is needed in event of an emergency of any kind, it automatically provides frequent verification of proper system operation as a by-product of the monitoring of subscriber home health parameter measurement activities.

Although the preceding description contains many specificities, these should not be construed as limiting the scope of the invention but as merely providing illustrations of some of the preferred embodiments of this invention. For example, a variety of subscriber remote station enclosure box designs could be used, including wall-mounted designs, designs having other shapes, integrated designs sharing cabinetry with miscellaneous healthcare equipment, etc. And although there are system reliability penalties, all alarm monitoring functions, including time window monitoring, could be performed by more complex alternative subscriber remote station embodiments. In particular, one or more health parameter monitoring devices and subscriber remote station functions could be combined in an integrated package. It would be very easy to incorporate all remote station functions, including all alarm monitoring functions, in a deluxe health parameter measurement device, which would plug into a telephone wall jack in an outpatient's home to enable communication with a central station. Also, the functions of the various components itemized in the preceding description might be largely combined in one PC board, different types of electrical switches could be used, etc. Thus the scope of the invention should be determined by the appended claims and their legal equivalents, rather than by the examples given.

I claim:

1. A home health parameter monitoring system for monitoring a subscriber's compliance with prescribed health parameter measurement activity regimen and for alarm-monitoring outcomes of said measurement activities via a communication link, comprising:

(a) a subscriber remote station for transmission of information corresponding to outcomes of said subscriber's health parameter measurement activities via said communication link, said subscriber remote station further comprising:

a signal interface means operative to accept predetermined health parameter measurement outcome signals generated by at least one interconnected health parameter measurement device in response to said subscriber's health parameter measurement activities, wherein said outcome signals signify whether said health parameter measurements are either "normal" or "in-alarm", as differentiated by predetermined alarm criteria, and a communicator means operative to be activated by said measurement outcome signals to responsively transmit corresponding predetermined health parameter measurement outcome messages via said communication link, (b) a central monitoring station for receiving said measurement outcome messages via said communication link, said central station further comprising:

a scheduler means operative to optionally preschedule periodic health parameter measurement time windows of the same or varying time width, one such time window for each of said subscriber's prescribed health parameter measurements, each said time window bounded by a unique opening time and a unique closing time specified by or for said subscriber; wherein said subscriber's compliance with prescribed health parameter measurement schedules can be inferred if either a valid "normal" or "in-alarm" health parameter measurement outcome message is transmitted from said subscriber's remote station to said central station via said communications link within each said prescheduled time window, and an alarm processor means operative to alarm-monitor said outcome messages for identification of said "in-alarm" messages, and to assure that at least one valid "normal" or "in-alarm" health parameter measurement outcome message is transmitted from said subscriber's remote station to said central station via said communication link within each said prescheduled time window, and a data storage means operative to store a data record of predetermined format for each said measurement outcome message.

2. The home health parameter monitoring system of claim 1, wherein said subscriber remote station further includes at least one help-button switch, which when actuated causes said communicator means to become operative to responsively transmit a predetermined alarm message to said central station via said communication link.

3. The home health parameter monitoring system of claim 1, wherein said subscriber remote station further includes a miniature radio receiver which receives RF signals of predetermined frequency from at least one miniature wireless help-button RF transmitter, and responsively activates said communicator means to become operative to responsively transmit a predetermined alarm message to said central station via said communication link.

4. The home health parameter monitoring system of claim 1, wherein said subscriber remote station further includes an auxiliary signal interface means operative to accept predetermined signals from other types of health care equipment, and to responsively cause said communicator means to become operative to responsively transmit predetermined messages to said central station via said communication link.

5. A home health parameter monitoring system for monitoring a subscriber's compliance with prescribed health parameter measurement activity regimen and for alarm-monitoring outcomes of said health parameter measurement activities via a communication link, comprising:

(a) a subscriber remote station for transmission of information corresponding to outcomes of said subscriber's health parameter measurement activities via said communication link, said subscriber remote station further comprising:

a signal interface means operative to accept predetermined measurement signals generated by at least one interconnected health parameter measurement device in response to said subscriber's health parameter measurement activities, wherein said measurement signals correspond to measured values of said health parameters, and a limit-setting means operative to accept entry of predetermined limit settings differentiating between "normal" and "in-alarm" values for said measurements, and a limit-check means operative to process said measurement signals to differentiate between "normal" and "in-alarm" measurements, and a communicator means operative to be activated by said measurement signals to responsively transmit a predetermined "normal" or "in-alarm" health parameter measurement outcome message for each said measurement signal via said communication link, (b) a central monitoring station for receiving said measurement outcome messages via said communication link, said central station further comprising:

a scheduler means operative to optionally preschedule periodic health parameter measurement time windows of the same or varying time width, one such time window for each of said subscriber's prescribed health parameter measurements, each said time window bounded by a unique opening time and a unique closing time specified by or for said subscriber; wherein said subscriber's compliance with prescribed health parameter measurement schedules can be inferred if either a valid "normal" or "in-alarm" health parameter measurement outcome message is transmitted from said subscriber's remote station to said central station via said communication link within each said prescheduled time window, and an alarm processor means operative to alarm-monitor said outcome messages for identification of said "in-alarm" messages, and to assure that at least one valid "normal" or "in-alarm" health parameter measurement outcome message is transmitted from said subscriber's remote station to said central station via said communication link within each said prescheduled time window, and a data storage means operative to store a data record of predetermined format for each said measurement outcome message.

6. The home health parameter monitoring system of claim 5, wherein said subscriber remote station further includes at least one help-button switch, which when actuated causes said communicator means to become operative to responsively transmit a predetermined alarm message to said central station via said communication link.

7. The home health parameter monitoring system of claim 5, wherein said subscriber remote station further includes a miniature radio receiver which receives RF signals of predetermined frequency from at least one miniature wireless help-button RF transmitter, and responsively activates said communicator means to become operative to responsively transmit a predetermined alarm message to said central station via said communication link.

8. The home health parameter monitoring system of claim 5, wherein said subscriber remote station further includes an auxiliary signal interface means operative to accept predetermined signals from other types of health care equipment, and to responsively cause said communicator means to become operative to responsively transmit predetermined messages to said central station via said communication link.

9. A home health parameter monitoring system for monitoring a subscriber's compliance with prescribed health parameter measurement activity regimen and for alarm-monitoring outcomes of said health parameter measurement activities via a communication link, comprising:

(a) a subscriber remote station for transmission of information corresponding to said subscriber's health parameter measurements via said communication link, said subscriber remote station further comprising:

a signal interface means operative to accept predetermined measurement signals generated by at least one interconnected health parameter measurement device in response to said subscriber's health parameter measurement activities, wherein said measurement signals correspond to said health parameter measured values, and a communicator means operative to be activated by said measurement signals to responsively transmit predetermined health parameter measurement messages via said communication link, (b) a central monitoring station for receiving said measurement messages via said communication link, said central station further comprising:

a limit-setting means operative to accept entries of predetermined limit settings differentiating between "normal" and "in-alarm" values for said health parameter measurements, and a scheduler means operative to optionally preschedule periodic health parameter measurement time windows of the same or varying time width, one such time window for each of said subscriber's prescribed health parameter measurements, each said time window bounded by a unique opening time and a unique closing time specified by or for said subscriber; wherein said subscriber's compliance with prescribed health parameter measurement schedules can be inferred if at least one valid health parameter measurement message is transmitted from said subscriber's remote station to said central station via said communication link within each said prescheduled time window, and an alarm processor means operative to alarm-monitor said measurement messages for identification of said "in-alarm" messages, and to assure that at least one valid health parameter measurement message is transmitted from said subscriber's remote station to said central station via said communications link within each said prescheduled time window, and a data storage means operative to store a data record of predetermined format for each said measurement message.

10. The home health parameter monitoring system of claim 9, wherein said subscriber remote station further includes at least one help-button switch, which when actuated causes said communicator means to become operative to responsively transmit a predetermined alarm message to said central station via said communication link.

11. The home health parameter monitoring system of claim 9, wherein said subscriber remote station further includes a miniature radio receiver which receives RF signals of predetermined frequency from at least one miniature wireless help-button RF transmitter, and responsively activates said communicator means to become operative to responsively transmit a predetermined alarm message to said central station via said communication link.

12. The home health parameter monitoring system of claim 9, wherein said subscriber remote station further includes an auxiliary signal interface means operative to accept predetermined signals from other types of health care equipment, and to responsively cause said communicator means to become operative to responsively transmit predetermined messages to said central station via said communication link.

* * * * *